United States Patent [19]

Ottes et al.

[11] Patent Number: 5,635,645
[45] Date of Patent: Jun. 3, 1997

[54] METHOD OF COMPRESSING DATA IN AN ULTRASONIC PIPE INSPECTION PROBE

[75] Inventors: Josef G. Ottes, Bruchsal; Helmut Stripf, Eggenstein-Leopoldshafen, both of Germany

[73] Assignee: Kernforschungszentrum Karlsruhe GmbH, Karlsruhe, Germany

[21] Appl. No.: 267,669

[22] Filed: Jun. 29, 1994

Related U.S. Application Data

[63] Continuation-in-part of PCT/DE92/01034 Dec. 11, 1992.

[30] Foreign Application Priority Data

Dec. 13, 1991 [DE] Germany .......................... 41 41 123.4

[51] Int. Cl.$^6$ .................................................. G01N 29/10
[52] U.S. Cl. ........................ 73/623; 364/571.04; 73/602
[58] Field of Search ...................... 73/623, 602; 364/506, 364/507, 508, 550, 571.02

[56] References Cited

U.S. PATENT DOCUMENTS

| 4,909,091 | 3/1990 | Ellmann ........................................ 73/623 |
| 4,953,405 | 9/1990 | Hara et al. .................................... 73/602 |

FOREIGN PATENT DOCUMENTS

| 3638936 | 5/1988 | Germany . |
| 93/12420 | 6/1993 | WIPO . |

OTHER PUBLICATIONS

DATACOM 4/91, "Daten–Kompression, Grundlagen und Übersicht", pp. 88–94, Apr. 1991.

*Primary Examiner*—Christine K. Oda
*Attorney, Agent, or Firm*—Klaus J. Bach

[57] ABSTRACT

In a method of compressing data obtained from ultrasonic propagation-time measurements made at a given pulse-repetition rate over a broad surface by an inspection probe which slides through the pipe in order to detect corrosion and other abnormalities in the pipe, the particular physical characteristics of the pipe are taken into consideration whereby a high data-compression factor and, for the subsequent analysis, reliable reproduction of the actual conditions in the pipe are achieved.

8 Claims, 3 Drawing Sheets

FIG. 2

| WALL DISTANCE WINDOWS: | 2 |
| WALL THICKNESS WINDOWS: | 3 |
| REFERENCE VALUE WALL THICKNESS: | 50 |

| SENSOR: | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| REFERENCE: WALL DISTANCE | 40 | 41 | 42 | 3F | 40 | 41 | 42 | 42 | 41 | 40 | 3F | 3C | 41 | 42 | 40 | 40 |
| MEASUREMENT VALUES: WALL DISTANCE | 3E | 3F | 40 | 41 | 40 | 41 | 41 | 40 | 43 | 44 | 45 | 46 | 48 | 4C | 44 | 42 |
| WALL THICKNESS | 50 | 51 | 51 | 50 | 51 | 50 | 51 | 50 | 4E | 4D | 4B | 4A | 47 | 44 | 49 | 4F |
| COMPRESSED: WALL DISTANCE | | | | | | | | 88 (MULTIPLICATION FACTOR 9) | | 44 | 45 | 46 | 48 | 4C | 44 | 42 |
| WALL THICKNESS | | | | | | | | 8A (MULTIPLICATION FACTOR 1 + 10) | 41 | 42 | 4A | 47 | 44 | 49 | 4F | |
| DECOMPRESSED: WALL DISTANCE | 40 | 41 | 42 | 3F | 40 | 41 | 42 | 42 | 41 | 44 | 45 | 46 | 48 | 4C | 44 | 40 |
| WALL THICKNESS | 50 | 50 | 50 | 50 | 50 | 50 | 50 | 50 | 50 | 50 | 4B | 4A | 47 | 44 | 49 | 50 |

COMPRESSION FACTOR + ( 2 × 16 ) / 14 = 2.28

(ALL NUMBERS IN HEXADECIMAL REPRESENTATION)

METHOD OF COMPRESSING DATA IN AN ULTRASONIC PIPE INSPECTION PROBE

The present application is a continuation-in-part of International application PCT/DE92/01034 filed Dec. 11, 1992, claiming priority of German application P 41 41 123.4 filed Dec. 13, 1991.

BACKGROUND OF THE INVENTION

The invention relates to a method of compressing data obtained from ultrasonic measurements made by an ultrasonic sonic pipe inspection probe which detects corrosion or other abnormalities in a pipe wall. The data are derived from ultrasonic propagation time measurements which are obtained by ultrasonic transducers combined in a module. The module or modules are disposed on predetermined circumferential areas of an ultrasonic pipe inspection probe with which they slide along the inner surface of a pipe to be checked. The ultrasonic transducers emit an ultrasonic pulse with a repetition frequency adjusted to the probe speed and receive the echo returned from the inner and outer surfaces of the pipe. By determining the travel time difference and taking into consideration the sound speed, the remaining thickness of the pipe can be determined over its whole surface. Because of the signal/statics ratio preferably the first received echoes are utilized.

The data derived from the measurements are recorded in a data storage during the travel of the ultrasonic inspection probe. However, the amount of data is very large. Without data compression the limits of the data storage are rapidly reached which substantially limits the travel distance of the ultrasonic inspection probe.

Normally, however, it can be assumed that the walls of a pipeline are essentially sound, that is, in good shape, over long distances. In those areas of course not all the measurements need to be stored but the tolerable measurement values can be replaced by a representative value. Upon retrieval of the data from the data storage after completion of the travel through the pipeline, the condition of the pipeline should be represented without any gaps.

DE 3638936 discloses a method wherein the data are compressed in such a way that measurement values deviating from a previous measurement value within a predetermined range (tolerance band) are only counted and recorded and stored by numbers. However, with the predetermined range this method does not or does not sufficiently reduce recording requirements when the wall thickness changes or the sensor mounting structure is worn, since, in those cases, the measurement values are outside the predetermined range. Furthermore, with this method the predetermined range may fall into a measurement value range which is important or corrosion determination whereby the quality of the quantitative corrosion determination is reduced.

Known methods of data compression are described and explained in DATACOM/91, pages 88 ff. The most suitable method is, or example, the Huffmann-coding (see page 94, columns 2 and 3 and page 96, columns 1 and 2). However, these methods do not take into consideration the physical laws of ultrasonics. Consequently no great savings are achieved therewith.

Ultrasonic data are recorded, for example, in a 12-bit data format. The first stage of the compression includes a data reduction. From the 12-bit data format the information is selected which is needed for later corrosion determination. For this a 7-bit data format is sufficient which is a subquantity of the 12-bit data format. This data format covers a defined value range with a predetermined resolution.

Each set of data comprising 64 advancement and wall thickness values entered into a compression computer is taken as a data set and compressed. The compression is based on the assumption that pipelines are free of corrosion over long distances and measurement values taken do not distinguish or are within a narrow tolerance band. This tolerance band is generated by arranging a window of predetermined width around a previously determined reference value. With the tolerance band the roughness of the wall and irregularities in the manufacture of the pipe are suppressed. By means of this tolerance and compression window the data are recorded with two different resolution ranges: a fine resolution for the corrosion areas and a rough resolution in the areas of normal wall thickness or nominal advancement.

The principle of the data compression method resides in the representation of multiple consecutive data, which are within the tolerance band, by means of a multiplier. The 7-bit data representation permits assignment of a special meaning to the eighth bit of a data word. The eighth bit is utilized as a prefix bit in order to be able to change the interpretation of the data word. The first seven bits may then contain a multiplier rather than a measurement value whereby it contains the number of measurement values which are within the predetermined tolerance range which are formed around the preassigned reference value. Maximally this may be 128 such values which corresponds to a binary representation of 7 bits. If a measurement value is outside the window, its value is fully recorded. The prefix bit is then not utilized. The multiplier count starts at 80H wherein 80H corresponds to a multiplier of 1. In the most advantageous case, when all measurement values are within the tolerance bands consequently only one byte with the value of 255 (=FFH) is recorded. It is the most disadvantageous case when all measurement values are outside the tolerance bands or one or more values outside the tolerance band are always followed by a value within the tolerance band. In both these cases, 128 bytes have to be recorded.

It is the object of the present invention to increase the data compression in the data storage of an ultrasonic pipe inspection probe so that it can pass through long stretches of pipelines without limitations and efficiently while the rough environmental conditions are particularly taken into consideration for data storage.

SUMMARY OF THE INVENTION

In a method of compressing data obtained from ultrasonic propagation-time measurements made at a given pulse-repetition rate over a broad surface by an inspection probe which slides through the pipe in order to detect corrosion and other abnormalities in the pipe, the data-compression factor is considerably increased compared with prior art methods. By taking into careful consideration the particular physical characteristics of the pipe, a high data-compression factor can be achieved during a run and, for the subsequent analysis, reliable reproduction ensured of the actual conditions in the pipe.

The measurement values for the advancement depend on the distance of the transducer carrier from the inner pipe wall, on the wear of the transducer carrier during probe advancement and on the condition of the inner wall of the pipeline stretch to be measured. Generally, for each transducer the base setting and the wear of the transducer carrier are different. Therefore a particular advancement reference value is assigned to each transducer. The reference value is formed by averaging which is maintained over the whole probe travel so that, with wear, the reference values are automatically continually adjusted.

For measurement of the wall thickness a single reference value is utilized for all transducers since all transducers normally are measuring walls of the same thickness. The wall thickness reference value is formed by the same continuous averaging. The tolerance band is defined by a reference value and a window which is symmetrically disposed around the reference value in predefined units.

An extended sequence of skips is represented by a multiplier: Then as prefix a data word is utilized to which a value is assigned (1) which makes no sense as a measurement value in connection with the measurements taken. For example, the measurement value "one" corresponds to a wall thickness of 0.2 mm or an advancement value of 0.34 mm. Such values cannot be measured for physical reasons.

If the compression of several consecutive data sets represents a sequence with optimal compression (=FFH) several data sets can be combined via one multiplier by means of a prefix byte which directly follows the synchronization bytes.

The compression actor is determined essentially by the data structure, which is much dependent on the measurement parameters and therefore is not predictable. In order to be able to better compress the data of various sensors which are in a sequence outside the tolerance band but which cannot be changed at that point the compression can be performed in two alternative stages. Stage 1 corresponds to the method described. In the second stage the respective previous measurement values of the same transducer are utilized as reference values, not the base reference values as utilized in the first stage. Measurement values within the tolerance band are represented by the reference value. If subsequent corresponding values differ they are fully (or by their difference) recorded; the same measurement values are described by a single multiplier. If differences are recorded, two consecutive identical measurement value differences can be defined by a single byte.

At the end of stage two it is determined on the basis of the achieved compression actor by which method the compressed data are recorded. The compressed data set is then provided with a corresponding marker. Since the method according to stage two requires a greater data storage security, this method is utilized only if data compression is substantially improved and with storage means having high data reliability.

At the end of a test run the ultrasonic data are evaluated. For this the data need to be decompressed. A multiplier is then replaced by the corresponding number of the respective reference values.

The gathering of the reference values is of particular importance. If possible, a situation has to be avoided wherein the tolerance band extends into the measurement value range of the corrosion areas since otherwise the quantitative determination of the corrosion areas will have insufficient resolution. The reference value for the wall thickness is found by arithmetic averaging of a defined number of data sets; it is therefore adjusted continuously to different wall thicknesses. Echo skips (measurement value 0) and range transgressions (measurement value 127) are disregarded for averaging. In order to avoid detrimental influences of far off-base measurement values on the averaging procedure, in the first stage only those values are utilized for averaging which are disposed within the predetermined window. If more values are disposed outside the window than within (for example, after a change of wall thickness) all values of the data set are utilized for averaging.

By the arrangement of the transducers which are displaced in longitudinal direction on the sensor carrier, a stepped function of the reference value can be obtained if the wall thickness changes are large relative to the tolerance band width. In order to avoid the need to accept in this area corrosion measurements with insufficient resolution the tolerance band is reduced for a short period if a change of wall thickness is recognized. Therefore the compression method must be designed to be able to tolerate errors.

The quantitative determination of interior corrosion on the basis of the advancement data is obtained by a relative measurement. Interior corrosion is always indicated by an increase in the wall distance measurement value (see FIG. 1). For the quantitative calculation two wall distance measurement values are subtracted. One measurement value corresponds to the wall distance value at the corrosion location. The second measurement value corresponds to the wall distance value in a defect-free pipe. For a defect-free pipe the wall distance value is given by the reference value. Consequently, the measurement values obtained at corrosion locations and during sensor carrier upliftings must be filtered out for the determination of the reference values for the wall distance. This is achieved by disregarding measurement values which are high relative to the instant reference value (as a result of corrosion or sensor carrier uplifts).

At the beginning of a test run the reference values are generated by averaging a predetermined number of data sets. The subsequent reference value calculations are performed during the data gathering and data compression procedures.

The data loss of particular information units suffered with each compression procedure results in substantially greater data losses or greater data misrepresentation after the decompression. This is particularly true for the data losses of reference values. In order to achieve the greatest possible security for the data storage the reference values are stored redundantly several times. At the beginning of a data block the reference values of the previous run are stored in two different data sets. They are then valid for the whole data block. Since the wall thickness reference value can change frequently the particular instant wall reference value is attached preferably to each tenth data set.

Because of the physical and technical limiting conditions in the ultrasound measurement of pipelines, there are for the data compression the following requirements:

as great a compression factor as possible;
resolution of the corrosion location measurement:
    0.2 mm or a wall thickness up to 25 mm,
    0.4 mm or wall thicknesses between 25 and
    50 mm for a preliminary run,
an algorithm which allows for rapid and error-free synchronization even with non-restitutable flawed band locations (error tolerance).

An embodiment of the invention is schematically shown in the drawings and will be described. First, however, an ultrasound measuring procedure is described or explanation and the flood of measurement values obtained during a test run is pointed out. The utility of data compression is apparent therefrom.

After completion of a probe passage the data are evaluated with the aid of a computer. For this purpose the data are decompressed. The pipe is straightened out in a plane herefor whereby each sensor appears to move in a straight line in the direction of the pipe axis. The measurement values obtained at the various points are indicated by different color representations (in FIG. 3 gray contrasts). In this manner a three-dimensional representation (C-scan) is achieved. For the quantitative determination of corrosion dimensions particular transducer data can be given in an x-y representation (B-scan).

BRIEF DESCRIPTION OF THE DRAWINGS

FIG. 2 an example of a compression of ultrasonic data derived from a 18-transducer probe.

DESCRIPTION OF A PREFERRED EMBODIMENT

For measuring the remaining wall thickness 1 of corroded pipelines the ultrasound system is employed in accordance with the principle of the ultrasound-travel time-procedure. The ultrasound impulse 2 emitted from a transducer 3 reaches the pipe wall 4 at a right angle. For each ultrasound impulse two travel times are determined, that is:

travel time between sending impulse and sound wall entrance impulse, travel time between sound wall entrance impulse and a first back wall echo or travel time in the back wall echo sequence.

Figure 1:
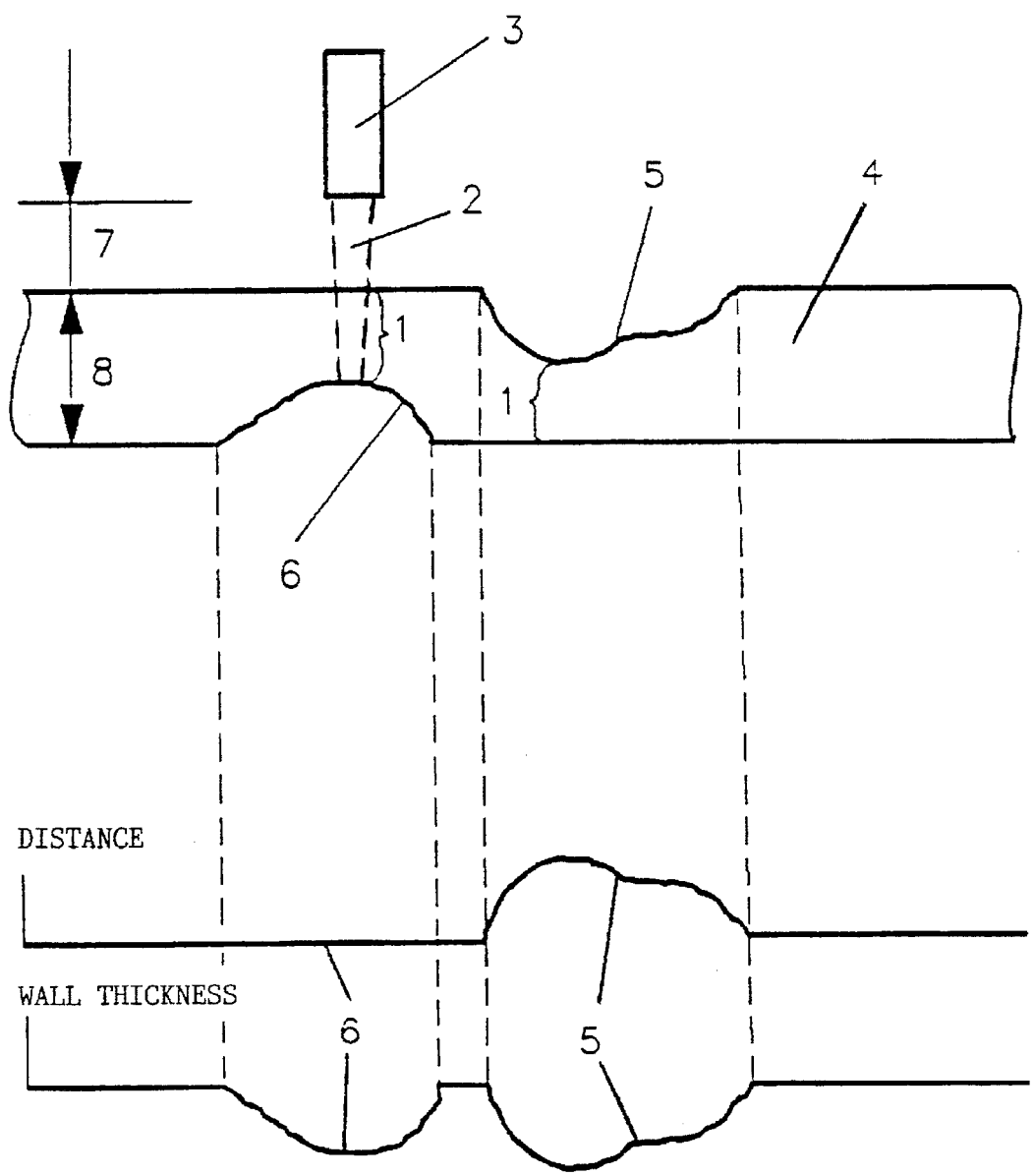
FIG. 1 the principle of ultrasonic (US) measuring and recording of the measuring process.

From the travel time difference between the front wall and the back wall echoes the remaining wall thickness is determined. FIG. 1 shows the measuring principle. From the distance 7 between transducer 3 and the adjacent pipe wall, some identification of the kind of corrosion can be made. With inside corrosion 5 the distance 7 becomes larger; if it does not change while the wall thickness 8 becomes smaller the defective area 6 is on the outside, that is, there is outside corrosion 6.

The inside corrosion 5 can correspondingly be determined by a change of the signal travel distance to the pipe wall and the wall thickness. The determination of the inside corrosion 5 via the signal travel distance is a relative measurement procedure whereas the wall thickness measurement is an absolute measurement procedure.

For physical reasons the impulse amplitude of the front wall echo is always greater than the impulse amplitude of the back wall echo. In highly corroded areas the ultrasound impulse is weakened and scattered so that often only the wall distance measurement can be performed.

Figure 3:
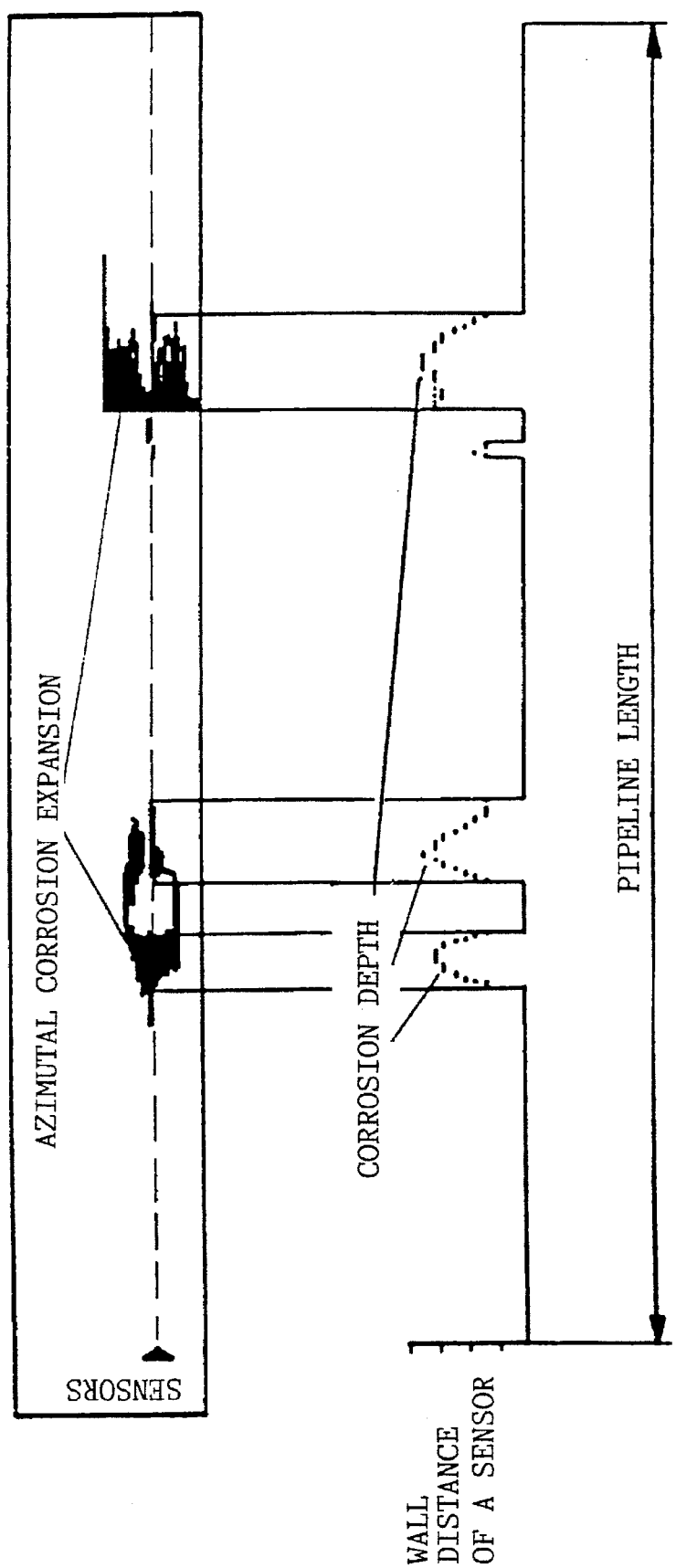
FIG. 3 the B- and C- scan representation of the wall distance data at a corrosion location with subsequent circumferential welding seam. The B-scan shows the wall distance reference value, the tolerance band and the measurement values required or the determination of the corrosion geometries.

In order to fully irradiate the pipe wall over its whole surface a number of transducers have to be provided circumferentially next to one another which corresponds to the surface area to be measured and all have to be energized one after the other for supplying the desired information. If, in the ultrasound signal generation, a repetition frequency that fits the probe travel speed is utilized, it is possible to achieve a gap-free examination also in longitudinal direction. Such an azimuthal and longitudinal recording of the wall conditions is shown in FIG. 3. The upper shade-like representation shows qualitatively the azimuthal condition of the pipe wall over the pipe length. The lower representation gives quantitatively the wall thickness along the sensor track indicated by the arrow. Values obtained by the coordination of the azimuthal or surface representation from the signals of the azimuthally distributed transducers and the signal representation from a particular transducer are indicated by dash lines. In a computer printout a quantification of the corrosion depth in the pipe wall can be achieved or azimuthal recording also by way of color tones.

The recorded measurement values have to be retained for later evaluation. This requires a storage memory with large storage capacity as can be seen from the estimation given below:

A pipe of 200 km length is to be checked out; it is assumed to have a diameter requiring 512 transducers evenly distributed over the circumference. If the probe is traveling at a speed of 1 m/sec and the ultrasonic transducers are energized with a frequency of 400 Hz the resulting data amount is:

| $N$ | = 512 | × 2 | × 400 | × 200,000 |
|---|---|---|---|---|
| Byte | Number of transducers | Front and rear wall | Repeat frequency, echo | Travel time at travel speed of 1 m/sec |
| | = 81.9 GByte | | | |

This amount or data cannot be directly recorded with presently available data storage systems given the probe body volume. However, as mentioned earlier, a pipeline will normally be sound over long distances and will not be corroded. It is therefore possible to utilize a data compression which greatly reduces the amount of information to be stored.

The ultrasonic measuring system is divided into modules with preferably 16, 32 or 64 transducers. Depending on the pipeline diameter up to 8 such modules are utilized. The individual transducers of a module are energized sequentially with a repetition frequency of up to 400 Hz.

The data of a transducer module are supplied to a compression computer where they are compressed and, tacked with a particular characterization, check sum and synchron marks, transferred to a register computer. The register computer combines the data of different compression computers to blocks of about 1.8 MByte length and deposits them in a predetermined format in a tape storage.

For a 64-transducer ultrasonic module a data set contains 64 wall distance and 64 wall thickness values. These data are taken by the compression computer and stored sequentially corresponding to the transducer number.

V1 j wall distance 1. transducer
W1 j wall thickness 1. transducer
V2 j wall distance 2. transducer
W2 j wall thickness 2. transducer
.
.
.
V64 j wall distance 64. transducer
W64 j wall thickness 64. transducer j=set number, counting from the beginning of data recording.

FIG. 2 shows an example of the compression procedure. The data set given consists at 16 value pairs. The wall distance window comprises 2 units, the wall thickness window comprises 3 units.

The savings for a data set with 2×z values which can be achieved with this compression procedure can be described by the following formula:

$$\text{Savings } E = \sum_{k=1}^{2} AK \times (k-1)$$

AK=number of groups with k values within the tolerance band

This formula shows that the savings are greatest when k is very large. When k=1 (Sequence: value outside, value within, value outside) no savings can be achieved. The maximum savings top a data set are 127.

The compression rate KG or an individual data set with $2 \times z$ values is calculated as $$KG = 2 \times z / (2 \times z - E).$$

It is for the most advantageous case: $KG = 2 \times z$.
For the example in FIG. 2 the savings are:

$$E = 1 \times (9-1) + 1 \times (11-1) + 1 \times (1-1) = 18$$

The compression rate is:

$$KG = 32/14 = 2.28.$$

In order to achieve the greatest possible savings physical relationships resulting from the ultrasonic technology and from the design of the transducer carrier are utilized in order to prepare the data optimally for the compression:

In the neighborhood of weld seams the transducer carrier is raised slightly; this results in an increase of the distance but does not change the wall thickness values. By reorganization of the data wherein first the distance data and then the wall thickness data are compressed the savings E can be increased.

In the areas of pipe installations and with soiling or failures of individual transducers no ultrasonic echo will be received or the wall distance nor for the wall thickness. The loss is indicated by the measurement value 0. With the loss of wall distance measurements no wall thickness echo can be received or physical reasons. Consequently the compression algorithm can consider the wall thickness value 0 as a value within the tolerance band and achieve thereby a higher, compression rate if the loss of wall distance measurements is recognized.

The compression procedure described is used for the testing of pipelines. The pipeline length to be measured in a test run was up to 200 km. On the average in about 70 test runs a compression actor of 8 was achieved. A data block with the compression actor 9 was, after decompression, compressed by means of the Huffmann method. In this manner only a compression actor of 4 was achieved.

LISTING OF REFERENCE NUMERALS

| | LISTING OF REFERENCE NUMERALS |
|---|---|
| 1 | Remaining wall thickness |
| 2 | Ultrasound impulse |
| 3 | Transducer |
| 4 | Pipe wall |
| 5 | Inside corrosion |
| 6 | Defect, outside corrosion |
| 7 | Distance |
| 8 | Wall thickness |

What is claimed is:

1. A method of compressing data collected by a measuring probe comprising an ultrasonic transducer module moving through a pipe for measuring pipe abnormalities by way of travel time measurements of ultrasound generated at a predetermined repetition frequency;

wherein the travel times of a pulse emitted by said probe's ultrasonic transducer module and a first echo impulse resulting from said pulse entering an adjacent wall are determined by said ultrasonic transducer module and from the time difference between said pulse emission and the return of the first echo impulse, the adjacent wall distance is determined;

and from the travel time difference between arrival of the first echo impulse, and the back wall echo, the remaining wall thickness is determined;

and wherein from particular measurement transducer data values of said probe which are within and outside of a predetermined tolerance band the data values are formed into the same data format wherein said data values are subjected to a decompressible compression to form datasets;

wherein the data values from the ultrasound travel time measurements for the adjacent wall distance and for the wall thickness are recorded in a data format;

wherein the data format contains a prefix bit, which is not activated when said measurement value is outside the tolerance band, and a data word assigned to the measurement value is recorded wherein, when at least two subsequent measurement values are within the tolerance band, said data word is set to be interpreted as a multiplier count for said data values in place of consecutive value recording, said method comprising the steps of:

when a change of wall thickness is recognized, narrowing the tolerance band for a short period to avoid a reduction of resolution of the measurements in an area of possible corrosion, representing a longer series of failure of said transducer by a multiplier and placing the prefix bit ahead of the value to which said measurement value is assigned, further compressing in a second stage of the compression, two or more subsequently compressed equal data sets by a characterizing word and a multiplier value, taking a measurement value skip of said transducer of a wall distance signal in connection with the measurements, as a failure to measure the wall thickness and indicating the wall thickness value to be within the tolerance range and consequently, compressible, providing for said transducer module a particular wall distance reference value which, during said probe travel, is constantly updated by continuous averaging of a predetermined number of wall distance values and which is several times redundantly stored, maintaining for the wall thickness measurements for said transducers module of said probe only one reference value, a wall thickness value, which during said probe travel is continuously updated by arithmetic averaging of a predetermined number of consecutive data sets so as to be adjusted smoothly to changing wall thicknesses and storing several times redundantly and including all values of a data set disposed outside the tolerance band in the averaging procedure when more values are outside the tolerance band than within, and disregarding said echo skips where the measurement values are equal to 0, in the averaging procedure for the reference values.

2. A method according to claim 1, wherein the tolerance band is defined by the wall distance reference value and a window of predetermined width which is symmetrically arranged therearound.

3. A method according to claim 2, wherein the width of the tolerance band is so selected that said band does not include the measurement value range of corrosion locations which, as a result of an advanced corrosion stage, have to be included in the measurement process.

4. A method according to claim 3, wherein, at the beginning of a test run, the reference values are generated by averaging a predetermined number of data sets and the reference value calculations are made in parallel with the date, collection and data compression procedures.

5. A method according to claim 4, wherein the reference values for the wall distance are stored before the start of a data block in two separate data sets and then are valid for the whole data block.

6. A method according to claim 5, wherein an updated wall reference value is provided or each tenth data set.

7. A method according to claim 6, wherein the compression of the data is performed in real time.

8. A method according to claim 1, wherein, after the step of taking a measurement skip value, an additional compression stage is done, wherein the reference values for the compression are derived from the timewise preceding data set, wherein, depending on the degree of compression, a decision is made which compression procedure is utilized for storing the data.

* * * * *